(12) United States Patent
Havlir et al.

(10) Patent No.: US 7,482,022 B2
(45) Date of Patent: Jan. 27, 2009

(54) PALATABLE CHEWABLE TABLET

(75) Inventors: Tanya Havlir, Amston, CT (US); Kasra Kasraian, Andover, MA (US)

(73) Assignee: Pfizer Inc., New York, NY (US)

( * ) Notice: Subject to any disclaimer, the term of this patent is extended or adjusted under 35 U.S.C. 154(b) by 773 days.

(21) Appl. No.: 10/404,964

(22) Filed: Apr. 1, 2003

(65) Prior Publication Data

US 2003/0215503 A1 Nov. 20, 2003

Related U.S. Application Data

(60) Provisional application No. 60/370,086, filed on Apr. 4, 2002.

(51) Int. Cl.
*A61K 9/24* (2006.01)
*A61K 9/20* (2006.01)
(52) U.S. Cl. ................... 424/472; 424/464; 424/465
(58) Field of Classification Search ............ 424/441, 424/465
See application file for complete search history.

(56) References Cited

U.S. PATENT DOCUMENTS

| 3,558,600 | A |  | 1/1971 | Geiszler et al. ............ 260/239 |
| 4,525,358 | A |  | 6/1985 | Baltes et al. ................ 514/255 |
| 4,650,663 | A |  | 3/1987 | Peters et al. ................ 424/484 |
| 6,027,746 | A | * | 2/2000 | Lech .......................... 424/455 |
| 6,270,790 | B1 |  | 8/2001 | Robinson et al. ........... 424/441 |
| 6,455,533 | B1 | * | 9/2002 | Fanara et al. ........... 514/255.04 |
| 6,699,502 | B1 | * | 3/2004 | Fanara et al. ................ 424/484 |
| 2002/0032217 | A1 |  | 3/2002 | Fanara et al. ................ 514/310 |
| 2003/0035839 | A1 | * | 2/2003 | Hirsh et al. |

FOREIGN PATENT DOCUMENTS

| EP | 0294993 | 12/1988 |
| EP | 0357369 | 3/1990 |
| WO | WO9202212 | 2/1992 |
| WO | WO9408551 | 4/1994 |

* cited by examiner

*Primary Examiner*—Humera N Sheikh
(74) *Attorney, Agent, or Firm*—Gregg C. Benson; Robert T. Ronau

(57) ABSTRACT

A palatable chewable tablet is described herein for oral administration of cetirizine dihydrochloride. The formulation is made more palatable by incorporating a combination of a grape flavoring agent with a vanilla flavoring agent.

1 Claim, No Drawings

PALATABLE CHEWABLE TABLET

CROSS-REFERENCE TO RELATED APPLICATIONS

This application claims benefit of provisional application No. 60/370,086 filed Apr. 4, 2002.

FIELD OF INVENTION

The present invention relates to an oral chewable tablet, in particular, a chewable tablet that provides a palatable taste to mask the bitter taste of a pharmaceutical agent contained therein.

BACKGROUND

Cetirizine is a generic name for 2-[2-[4-[(4-chlorphenyl)phenylmethyl]-1-piperazinyl]ethoxy]-acetic acid and is typically provided as a dihydrochloride salt. Cetirizine is an orally active and selective H1-receptor antagonist currently prescribed for the treatment of seasonal allergies in patients aged 2 years and older. The current commercial products (Zyrtec™) are available as a white, film-coated, immediate release oral tablet in 5 and 10 mgA strengths and a sweet flavored syrup containing cetirizine hydrochloride at a concentration of 1 mg/ml for pediatric use. European patents Nos. 058,146; 294,993; and 357,369; and also WO 92/02212 describe cetirizine formulations for the controlled or continuous release of cetirizine in the form of tablets and capsules. Oral formulations in the form of a cough syrup are disclosed in WO 94/08551.

For patients, such as children, who have difficulty swallowing conventional tablets or capsules, chewable tablets are widely used in the pharmaceutical industry. In addition, chewable tablets avoid mishaps that may occur with liquids, such as spillage and stains.

One of the drawbacks to oral delivery systems however, is the situation where the drug to be administered is bitter, bad-tasting, odorous or in some manner unpleasant especially to children. Many efforts have been made in the past to "taste mask" these compounds either through elaborate flavor and/or sweetener delivery systems, adsorption of the drug within another material or by encapsulation with a polymer, fat, carbohydrate or other like material. These taste-masking methods basically prevent the bitter tasting components of the drug from contacting the taste-buds during oral ingestion yet break down and release the active upon dissolution in the stomach.

For example, U.S. Pat. No. 4,650,663 discloses the preparation of an oral pharmaceutical delivery system in which an unpleasant tasting anti-tussive such as noscapine, carbetapentane citrate or clophedianol hydrochloride is adsorbed onto magnesium silicate flakes and incorporated into a chewable tablet or lozenge. The adsorbate allegedly masks the bitter taste to an almost negligible level to encourage better patient compliance.

U.S. Pat. No. 6,027,746 discloses a soft chewable gelatin capsule having incorporated therein a drug dispersed in an oral suspension comprising a medicament adsorbate which masks bitter or bad-tasting pharmaceutical actives (such as antihistamines, decongestants and the like).

U.S. Pat. No. 6,270,790 discloses a soft, convex-shaped compressed chewable tablets. Active agents having a bitter or bad taste are masked by coating the drug with a 90:10 to 50:50 polymer blend of cellulose acetate or cellulose acetate butyrate and polyvinyl pyrrolidone or hydroxypropyl cellulose. However, coatings require an additional manufacturing step which adds to the manufacturing costs of the tablet.

U.S. Pat. No. 3,558,600 describes a method for masking the bitter taste of antihistamines belonging to the family of substituted 1-(p-chloro-benzhydryl)-piperazine. This method consists of transforming the active substance in the form of a free base into its long-chain alkyl sulfate salt, such as stearyl sulfate.

Another known method for masking the taste of active ingredients consists of forming an inclusion complex between the active ingredient and a cyclodextrin. In this case, the masking of the taste results from the trapping of the active ingredient, which cannot be released while it is in the mouth. The use of beta-cyclodextrin with cetirizine is described in WO 99/01133.

There still exists a need for a palatable formulation for cetirizine medicaments that assist in compliance especially with children.

SUMMARY

The present invention provides a palatable chewable tablet comprising cetirizine or a pharmaceutically acceptable salt thereof (preferably, the dihydrochloride salt), a sweetener (e.g., acesulfame potassium), a combination of a grape flavoring and a vanilla flavoring in a ratio from about 4:1 to 2:1 (preferably in a ratio from about 3:1 to about 2:1), a cyclodextrin (preferably β-cyclodextrin), and one or more additional excipients (e.g., magnesium stearate, colloidal silicon dioxide, anhydrous lactose, microcrystalline cellulose, microcrystalline cellulose modified with guar gum, croscarmellose sodium, mannitol, sucrose, and dextrinized sucrose).

In a preferred embodiment, a palatable chewable bi-layer tablet is provided comprising (a) a first layer comprising cetirizine or a pharmaceutically acceptable salt thereof (preferably, cetirizine dihydrochloride), a combination of a grape flavoring and a vanilla flavoring in a ratio from about 4:1 to 2:1, beta-cyclodextrin, colorants, one or more additional excipients (e.g., magnesium stearate, colloidal silicon dioxide, anhydrous lactose, microcrystalline cellulose, microcrystalline cellulose modified with guar gum, and croscarmellose sodium); and (b) a second layer comprising mannitol or dextrinized sucrose, a combination of a grape flavoring and a vanilla flavoring in a ratio from about 4:1 to 2:1, colorants, and one or more additional excipients (e.g., magnesium stearate).

DETAILED DESCRIPTION

The present invention relates to a cetirizine tablet that is more palatable for children to encourage better compliance with the physician's recommendations for treatment. Cetirizine is a very bitter tasting drug thus making it difficult to entice children to take the medication. Marketing studies have shown that children 5-12 years of age prefer grape flavors. However, Applicants have discovered that the addition of a vanilla flavoring agent in combination with the grape flavoring agent enhances the grape flavor thus making the tablet even more palatable, especially for children.

Suitable grape-flavoring agents include both natural and artificial flavoring agents and are generally available through several custom manufacturers around the world such as Givaudan (Vernier, Switzerland), Ungerer & Company (Lincoln Park, N.J.), and International Flavors & Fragrances (New York, N.Y.) to name a few. Those skilled in the art will recognize that there are several commercial sources available including custom blenders. A preferred grape flavoring system is Artificial Grape Flavor 486939 from Givaudan. Suitable vanilla-flavoring agents include both natural and synthetic flavoring agents and are available from manufactures around the world such as CHR Hansen, Inc. (Milwaukee, Wis.), Givaudan (Vernier, Switzerland), Ungerer & Company (Lincoln Park, N.J.) and International Flavors & Fragrances (New York, N.Y.) to name a few. Those skilled in the art will recognize that there are several commercial sources available including custom blenders. A preferred vanilla flavoring agent is PharmaSweet Powder Vanilla Flavor Enhancer from CHR Hansen, Inc. The weight ratio of grape to vanilla flavorings is generally in the range from about 4:1 to 2:1, preferably from about 3:1 to about 2:1. The flavoring agents are generally present in the tablet in an amount from about 0.2% to about 1.0%, preferably from 0.3% to about 0.4% by weight. Those skilled in the art will appreciate that the exact amount will vary depending upon the strength of the particular flavoring agent(s) used and will know how to adjust the concentration to achieve the appropriate level of taste. The amount of a particular flavoring agent used may also be limited by the concentrations approved by the regulatory agency (i.e., U.S. Food & Drug Agency) for use in pharmaceutical products. The grape and vanilla flavorings may be blended prior to addition to the pharmaceutical composition or added separately.

Cetirizine belongs to family of substituted benzhydryl piperazines, such as 2-[2-[4-[(4-chlorophenyl)phenylmethyl]-1-piperazinyl]ethoxy]ethanol (hydroxyzine), 2-[2-[4-bis(4-fluorophenyl)methyl]-1-piperazinyl]ethoxy]acetic acid (efletirizine), 1-[(4-chlorophenyl)phenylmethyl]-4-[(3-methylphenyl)-methyl]piperazine (meclizine), or 1-[(4-tert-butyl phenyl)methyl]-4-[(4-chlorophenyl)phenylmethyl]piperazine (buclizine), their optically active isomers, as well as their pharmaceutically acceptable salts. Accordingly, it will be appreciated by those skilled in the art that the present invention may be useful with any of the above-referenced cetirizine family members as well as cetirizine and its pharmaceutically acceptable salts. The amount of cetirizine present in the tablet will vary depending upon the particular dosage requirements. Generally, cetirizine is present in an amount from about 2.0% to about 2.5% by weight of the tablet for a 5 mgA or 10 mgA tablet.

It will also be appreciated by those skilled in the art that the present invention may be useful for other bitter tasting pharmaceutically active ingredients, especially antihistamines and decongestants well-known to those skilled in the art.

The composition may also contain colorants to improve the appearance of the tablet especially since an attractive coloration imparted by a colorant may improve patient compliance. In the present invention, blue and red pigments are typically used to achieve a purple color to match the grape flavoring. The relative amounts of the blue and red colorants will vary depending upon the particular hue of the individual colorants and the resultant purple shade desired. Generally, any red, blue, or purple colorant (natural or synthetic) may be used that is acceptable for use in pharmaceuticals by the regulatory authorities.

Any standard pharmaceutically acceptable excipient can be used in the chewable tablet formulation which provides adequate compression such as diluents (e.g., mannitol, sorbitol, lactose, sucrose, and compressible sugars such as DiPac™ (dextrinized sucrose), available from Austin Products Inc., Holmdel, N.J.), splitting or swelling agents (e.g., polyvinyl polypyrrolidone, croscarmellose sodium (e.g., Ac-Di-Sol™ available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, Philadelphia, Pa.), lubricating agents (e.g., magnesium stearate), and flow agents (e.g., colloidal silicon dioxide, such as Cab-O-Sil M5 available from Cabot Corporation, Kokomo, Ind.).

Sweeteners are often used to impart a pleasant flavor to the composition. Suitable sweeteners for use in the present invention include natural sweeteners such as sucrose, dextrose, fructose, invert sugar, mannitol, sorbitol, and the like, as well as synthetic sweeteners such as saccharin, aspartame, acesulfame potassium, cyclamates, and other commercial artificial sweeteners well-known to those of skill in the art. A preferred sweetener is acesulfame K (Sunett™ available from Nutrinova, Frankfort, Germany). The sweetener is added in an amount to achieve a desired sweetness. Typically, the sweetner is present in an amount from about 1.0% to about 5.0%. Those skilled in the part will appreciate that the amount of sweetener may vary depending on the strength of the particular sweetener used and the levels approved by the regulatory authorities for use in pharmaceutical products.

Suitable cyclodextrins for use in the present invention include α, β, or γ cyclodextrins, or an alkylated or hydroxy-alkylated derivatives thereof, such as heptakis (2,6-di-o-methyl)-β-cyclodextrin (DIMEB), randomly methylated β-cyclodextrin (RAMEB), and hydroxypropyl β-cyclodextrin (HPβCD). A preferred cyclodextrin is β-cyclodextrin (available from Cerestar USA, Inc., Hammond, Ind. or from Roquette America, Inc., Keokuk. Iowa under the tradename Kleptose™). If desired, the complex of the active substance with cyclodextrin can be prepared in advance, for example, by malaxating the active substance and the cyclodextrin in the presence of water, or by preparing an aqueous solution containing the active substance and the cyclodextrin in the desired molar ratio. Alternatively, the active substance and the cyclodextrin can be simply mixed with other excipients and adjuvants. The molar ratio of active substance to cyclodextrin is preferably from about 1.0 to about 4.0.

A typical manufacturing process for making either a single layer or bi-layer generally involves blending of the desired ingredients to form a uniform distribution of the cetirizine, colorants and flavoring agents. If desired, an inclusion complex of the cetirizine and cyclodextrin (e.g., β-cyclodextrin) may be formed prior to blending into the mixture by malaxating the cetirizine and cyclodextrin in the presence of water in a planetary mixer for about 20 minutes. The mixture is then dried in a drying oven. After drying, the complex is mixed with the color/flavoring blend. The blend is then compressed into a single layer or bi-layer tablet using standard methods well-known to those skilled in the art (e.g., Kilian T-100 tablet press or Courtoy 292/43 rotary bi-layer press). Preferably, excipients having hydroxy groups (e.g., mannitol) that are capable of forming esters with the cetirizine are separated from the cetirizine to avoid formation of cetirizine esters. Therefore, the preferred dosage form is a bi-layer construction where the cetirizine is in a separate layer from sugars such as mannitol. The colorants and flavoring agents may be added to both layers to form a uniform presentation of the tablet.

The tablets may be stored in glass or high density polyethylene (HDPE) bottles with or without a heat induced sealed (HIS) bottle. The bottle may also contain a dessicant. Alternatively, the tablets may be encapsulated into blister packs using standard methods well-known to those skilled in the art.

The following example is provided in order to better teach and disclose a specific embodiment of the present invention and the manner in which the chewable tablets of the present invention may be prepared. Those skilled in the art will recognize that the example is for illustrative purposes only, and that certain variations and changes may be made to alter these formulations in minor degrees. Such variations are still considered to fall within the spirit and scope of the present invention as recited by the claims herein below.

EXAMPLES

Cetirizine Bi-Layer Chewable Tablet:

A bi-layer chewable tablet was prepared using the following two formulations which were prepared separately and then compressed on a bi-layer tablet press.

Formulation 1: Active Layer

| Component | % by tablet wt |
| --- | --- |
| Cetirizine 2HCl | 2.22 |
| Betadex, Kleptose ™ 200F | 18.33 |
| Acesulfame K | 0.78 |
| Colloidal Silicon Dioxide | 0.24 |
| Microcrystalline Cellulose | 9.75 |
| Artificial Grape Flavor 486939 (Givaudan Roure) | 0.13 |
| Pharma Sweet FL PWD Nat (K) | 0.04 |
| Lactose monohydrate | 12.22 |
| Dye: Carmine ground #09349* | 0.05 |
| Dye: FD&C Blue #2 aluminum lake* | 0.05 |
| Magnesium Stearate | 0.61 |

Formulation 2: Placebo Layer

| Component | % by tablet wt |
| --- | --- |
| Mannitol | 53.60 |
| Acesulfame Potassium | 1.04 |
| Artificial Grape Flavor 486939 (Givaudan Roure) | 0.17 |
| Pharma Sweet FL PWD Nat (K) | 0.06 |
| Dye: Carmine ground #09349* | 0.07 |
| Dye: FD&C Blue #2 aluminum lake* | 0.07 |
| Magnesium Stearate | 0.56 |

*Available from Warner-Jenkinson, South Plainfields, New Jersey.

What is claimed is:

1. A palatable chewable bi-layer tablet comprising
   (a) a first layer comprising cetirizine dihydrochloride, betacyclodextrin, acesulfame K, colloidal silicon dioxide, microcrystalline cellulose, artificial grape flavor 486939, Pharma Sweet FL Pwd Nat(K), lactose monohydrate, Carmine Dye #09349, FD&C Blue Aluminum Lake and magnesium stearate; and
   (b) a second layer comprising mannitol, acesulfame K, artificial grape flavor 486939, Pharma Sweet FL Pwd Nat(K), Carmine Dye #09349, FD&C Blue Aluminum Lake and magnesium stearate;
   wherein the percent by tablet weight of each ingredient in said first layer is cetirizine dihydrochloride, 2.22%; betacyclodextrin, 18.33%; acesulfame K, 0.78%; colloidal silicon dioxide, 0.24%; microcrystalline cellulose, 9.75%; artificial grape flavor 486939, 0.13%; Pharma Sweet FL Pwd Nat(K), 0.04%; lactose monohydrate, 12.22%; Carmine Dye #09349, 0.05%; FD&C Blue Aluminum Lake, 0.05%; and magnesium stearate, 0.61%; and the percent by tablet weight of each ingredient in said second layer is mannitol, 53.60%; acesulfame K, 1.04%; artificial grape flavor 486939, 0.17%; Pharma Sweet FL Pwd Nat(K), 0.06%; Carmine Dye #09349, 0.07%; FD&C Blue Aluminum Lake, 0.07%; and magnesium stearate, 0.56%.

* * * * *